United States Patent
Reddy et al.

[19]

[11] Patent Number: 5,876,990
[45] Date of Patent: Mar. 2, 1999

US005876990A

[54] BIOCHEMICAL MEDIA SYSTEM FOR REDUCING POLLUTION

[76] Inventors: Malireddy S. Reddy; Syama M. Reddy, both of 78 Cherry Hills Farm Dr., Englewood, Colo. 80110

[21] Appl. No.: 731,886

[22] Filed: Oct. 22, 1996

[51] Int. Cl.$^6$ .............................. C12N 11/02; C02F 3/34; C12S 13/00; A23B 7/10
[52] U.S. Cl. .......................... 435/177; 435/262; 210/606; 210/632; 210/611; 252/180; 252/181; 426/53
[58] Field of Search ..................................... 210/606, 610, 210/611, 627, 631, 632; 252/176, 180, 181, 186.41; 426/52–54, 63, 64; 435/175–179, 264, 262, 267

[56] References Cited

U.S. PATENT DOCUMENTS

| | | | |
|---|---|---|---|
| 3,635,797 | 1/1972 | Battistoni et al. | 210/606 |
| 3,919,048 | 11/1975 | Dahlmans et al. | 435/177 |
| 4,043,869 | 8/1977 | Barker et al. | 435/177 |
| 4,232,044 | 11/1980 | Chiba et al. | 426/52 |
| 4,478,683 | 10/1984 | Orndorff | 210/632 |
| 4,588,506 | 5/1986 | Raymond et al. | 210/606 |
| 4,996,062 | 2/1991 | Lehtonen et al. | 426/52 |
| 5,051,184 | 9/1991 | Taylor | 210/632 |
| 5,464,766 | 11/1995 | Bruno | 210/632 |
| 5,503,766 | 4/1996 | Kulperger | 210/606 |

*Primary Examiner*—Thomas G. Wyse
*Attorney, Agent, or Firm*—Kyle W. Rost

[57] ABSTRACT

A first media provides an oxygen inducer such as catalase, bound and stabilized in pellet form so as to dissipate slowly into aqueous surroundings. A second media provides an oxygen supplier such as a peroxide, stabilized by combination with a proteinaceous compound such as urea and bound in a matrix that limits oxygen release. The two media are combined in aqueous environment to generate nascent oxygen at a modulated rate such that the oxygen is efficiently absorbed into the surrounding aqueous environment, promoting growth of aerobic species and reducing biological pollution. Specific adaptations demonstrate benefits of use in shrimp or fish ponds, raw milk, fruit juice, fresh food, silage and animal feed, fertilizer, plumbing systems, and grease traps. When used in ponds, further adaptations reduce algae and phytoplankton populations.

44 Claims, No Drawings

BIOCHEMICAL MEDIA SYSTEM FOR REDUCING POLLUTION

TECHNICAL FIELD

The invention generally relates liquid purification, and more specifically to reducing pollution through production of nascent oxygen at the bottom of ponds by the action of enzymes on oxygen yielding substrates. Further, the invention relates to production of oxygen in aquatic feeds, raw milk and other foods, animal feeds, fertilizers, plumbing compounds, sewage treatments, and polluted ponds and streams.

BACKGROUND ART

Bacterial systems have been used for liquid purification, to consume wastes and reduce pollution. Microbial systems are used to process sludge by anaerobic treatment, followed by aerobic treatment. The microorganisms often receive ancillary growth medium, and it is known to add selected enzymes to benefit microbial action. However, polluted water is found outside the environment of a sludge treatment pond or tank, and the techniques used on sludge are not practical or useful in open waters. It would be desirable to treat many types of polluted waters with the combination of micro-organisms and oxygen yielding substrates, to generate nascent oxygen and thereby inactivate pollution-creating, pathogenic, anaerobic micro-organisms.

Hydrogen peroxide has been used to sterilize fluids or liquids. However, hydrogen peroxide is soluble in water and disburses readily, which has limited its use to situations in which an entire body of water must be treated. The use of hydrogen peroxide has not been practical in large scale situations, since achieving an effective concentration throughout a large body of liquid is cost prohibitive and environmentally unsound. Even when pollution is localized to a limited area or strata of a large body of water, it has not been possible or practical to treat the limited, polluted area without also treating the entire body. It would be desirable to have a stable, sinkable, solid hydrogen peroxide or other oxygen generating substrate based system, such that the oxygen generating system can be locally applied to reduce pollution.

Pollution produces low oxygen levels at the bottom of commercial fish and shrimp ponds, which leads to special problems. One of the major causes of pollution in a shrimp pond is feed and waste. Shrimp tend to stay at the bottom of the pond, where pollution accumulates. Due to low oxygen content at the bottom of ponds, anaerobic micro-organisms grow on the nutrients from the shrimp feed. Anarobes can cause bacteriological and viral diseases. Further, if the oxygen level in shrimp ponds is not maintained at least at 3 to 5 ppm, shrimp will not grow to their full potential. If the concentration goes below 2.0 ppm, they will die within a few hours.

Another problem is the presence of excess algae, microflora and organic matter in pools, ponds, septic systems, wetlands and plumbing systems. While filtration and chemicals are effective against these problems, these measures are expensive and may lead to environmental problems. It would be desirable to have an effective, more problem free, biological or biochemical system that could eliminate the growth of pathogenic bacteria and unwanted micro-flora in swimming pools and ponds. Similarly, septic systems and grease traps become clogged with organic wastes. It would be desirable to have an effective biological system to eliminate such septic clogging.

Numerous types of hydrocarbon contamination are a further environmental and public health problem. Aerobic organisms are effective against hydrocarbons, but when the contamination is underground, aerating the ground to supply adequate oxygen to the micro-organisms is not economical. It would be desirable to reduce hydrocarbon pollution through a more effective biological system, without having to remove contaminated ground or mechanically aerate the subsurface areas.

Feed lots, dairy barns, poultry houses, and pig pens produce severe odors, which can prevent the animals from consuming enough ration. It would be desirable to have an effective and efficient biological system for reducing such odors.

To achieve the foregoing and other objects and in accordance with the purpose of the present invention, as embodied and broadly described herein, the product of this invention may comprise the following.

DISCLOSURE OF INVENTION

Against the described background, it is therefore a general object of the invention to provide an improved bacterial composition that, upon contact with water, will generate nascent oxygen at a gradual rate. Such oxygen generates at a rate that allows its absorption in water, resulting in elevated oxygen levels that are harmful to pollution creating anaerobic bacteria, while being highly beneficial to aerobic bacteria and other aerobic aquatic animals.

Another object is to create shelf-stable oxygen generating, bacterial composition that can be transported and stored with relative ease.

Another object is to create sinkable oxygen generating, bacterial composition that can reach the bottom of deeper ponds and create nascent oxygen, thus oxygenating the bottom of the ponds to retard the anaerobic bacteria and enhance the growth of aerobic bacteria.

Another object is to provide a stable system in which oxygen bearing compounds such as hydrogen peroxide will remain stable in storage over a long period.

Another object is to create a dry, hydrogen peroxide containing composition in which hydrogen peroxide will remain stable even upon contact with water.

Another object is to create an oxygen generating composition that is non-toxic to aquatic or marine animals, such as shrimp, fish, lobster, and crayfish.

Another object is to provide an oxygen generating composition that continuously generates oxygen upon contact with microbial or animal catalase, over a prolonged period, so that the composition will maintain high dissolved oxygen levels in a suspending medium for a prolonged period of time.

Another object is to provide an oxygen generating, safe, bacterial and biochemical composition that reduces foul odors due to hydrogen sulfide, and the like.

Another object is to provide an oxygen generating, bacterial composition that reduces suspended solids, COD, BOD, and the like.

Another object is to provide an oxygen generating, bacterial and biochemical composition that reduces sewer and plumbing problems and reduces grease accumulations in grease traps.

Another object is to provide a food grade oxygen generating, bacterial composition that reduces spoilage of raw milk, fruit juices, shrimp, fish, meat and other foods, especially during storage and transportation.

Another object is to provide a bacterial composition that, when applied in the ponds, retards growth of algae.

Another object is to provide an oxygen generating, bacterial composition that has value as fertilizer or as part of a fertilizer or soil conditioner.

Another object is to provide an oxygen generating, bacterial composition useful in hydroponic gardening to supply nutrients and oxygen to roots, thus eliminating the necessity of pumping air using mechanical sources and eliminating mechanical lifting of the plants off the water medium to expose the roots to air.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

According to the invention, a moisture activated biochemical media system that reduces biological pollution and spoilage contains a first media preparation of a moisture activated composition for supplying a predetermined, water dispersible oxygen inducer and a first carrier that carries the composition for supplying the predetermined oxygen inducer. A second media preparation of the system contains a biochemical oxygen-releasing composition that is reactive with the predetermined oxygen inducer in the presence of moisture for releasing nascent oxygen.

The following description serves to explain the principles of the invention.

BEST MODE FOR CARRYING OUT THE INVENTION

The invention is a biochemical media system that employs two compositions that interact to reduce biological pollution and spoilage. The first composition, termed "micro-prep," is the combination of a moisture activated means for supplying a predetermined, water dispersible oxygen inducer, plus a carrier means. The oxygen inducer may be catalase enzyme or other water soluble peroxide destabilizing compounds or enzymes, or combinations of these. The micro-prep may contain micro-organisms that produce the desired enzymes, or it may contain the desired enzymes themselves, or it may contain both micro-organisms and enzymes. Some of the micro-organisms may be non-producers of the oxygen inducer but are included for the benefits of other metabolic functions. Typically, the micro-prep is composed of bacteria and enzymes, in combination with the carrier material. Depending upon the specific application, the carrier may contain any of various binders, fillers, nutrients, preservatives, and high density ballast of specific gravity sufficiently greater than water to enable the micro-prep to sink in water.

The second composition, termed "oxy-prep," is a biochemical oxygen-releasing means. The oxy-prep is stable for dry storage and is not activated to release substantial oxygen even when wet, unless activated by reactive contact with the oxygen inducer. Typically, the oxy-prep is composed of a peroxide, such as hydrogen peroxide; a stabilizer such as urea, which interacts with hydrogen peroxide to form a stable carbamamide compound; an emulsifier such as lecithin; and a gum, such as guar gum, which controls oxygen release by establishing a porous matrix. The oxy-prep may include a carrier of ballast material of high specific gravity to enable the oxy-prep to be sinkable in water, in those uses where sinkability is desired. The components in oxy-prep are selected to preserve its function. Thus, the oxy-prep ballast material is preferred to be free of metals, which might induce unwanted release of oxygen. Preferred compositions and representative procedures for preparation are as follow:

COMPOSITION OF MICRO-PREP

The micro-organisms in micro-prep may be obtained from purified single or unpurified mixed strains, including mixed strains from compost origins. These bacteria are categorized in two groups. One is the catalase positive group, the other is the catalase negative group, with or without the capability of producing detectable quantities of hydrogen peroxide. Catalase positive, non-pathogenic, defined and undefined micro-organisms used in this invention are:

1. Members of the genus Propionibacterium; *Propionibacterium shermanii, Propionibacterium arabinosum, Propionibacterium zeae, Propionibacterium petersonii, Propionibacterium jensenii,* and *Propionibacterium pentosaecium;*
2. Non-pathogenic members of the genus Bacillus such as *Bacillus subtilus, Bacillus licheniformis, Bacillus polymyxa,* their spores, and the like.;
3. Strains of *Brevibacterium linens;*
4. Non-pathogenic molds belonging to the genera Penicillium, such as *Penicillium roquefortii, Penicillium camembertii,* and the like;
5. White non-pathogenic molds;
6. Catalase positive non-pathogenic micro-organisms present in animal and vegetable compost, and catalase positive non-pathogenic saprophytic soil microorganisms.

The catalase negative, non-pathogenic, defined and undefined strains of micro-organisms, with and without the capabilities of producing detectable amounts hydrogen peroxide, used in this invention are:

1. *Lactobacillus lactis, Lactobacillus bulgaricus, Lactobacillus salivarius, Lactobacillus casei, Lactobacillus plantarum, Lactobacillus acidophilus, Lactococcus lactis* var *lactis, Lactococcus lactis* var *cremoris, Lactococcus lactis* var *lactis* subspecies *diacetylactis;*
2. *Streptococcus faecalis, Streptococcus faecium, Streptococcus liquifaciens, Streptococcus thermophilous;*
3. *Leuconostoc mesenteroides* ssp *cremoris, Leuconostoc mesenteroides* ssp. *dextranicum;*
4. *Pediococcus acidolactici, Pediococcus pentosaecium, Pediococcus cerevisiae;*
5. Beneficial members of the genus Bifidobacterium, such as *Bifidobacterium bifidus* and *Bifidobacterium longum;*
6. Members of the genus Pseudomonas such as *Pseudomonas fragii, Pseudomonas denitrificans, Pseudomonas fluorescence;*
7. Beneficial members of the genus Aerobacter and Achromobacter;
8. Members of the genus Nitrosomonas, Nitrosococcus, Nitrobacter, Rhizobium, and Thiobacillus;
9. Catalase negative non-pathogenic micro-organisms present in animal and vegetable compost; and catalase negative non-pathogenic saprophytic soil microorganisms.

Procedure for preparing catalase positive organisms

The aforementioned catalase positive beneficial non-pathogenic micro-organisms are transferred three times, in sterile tryptic soy broth, prior to inoculating bulk medium. The composition of bulk medium for growing the catalase positive organisms is presented in Table 1. The medium is reconstituted at 12.0% solids level by blending with clean potable water. The initial pH of the medium is adjusted to 6.8 to 7.0 and heated to 170° F. to 212° F. and held at that temperature for a period of 2 minutes to 1 hour. After the heat treatment, the medium is cooled to 80° to 100° F. and inoculated with appropriate catalase positive organism(s). The organisms are allowed to grow until pH comes down to between 5.0 to 5.75. At this stage, the culture is neutralized to pH 7.0 using a suitable basic neutralizer such as sodium hydroxide, potassium hydroxide, magnesium hydroxide, ammonium hydroxide, gaseous ammonia or mixtures thereof. The culture is allowed to grow again until pH comes down to 5.0 to 5.75. The neutralization is continued until the culture can no longer grow, which is an indication that the nutrients are exhausted. At this stage the culture is cooled to 40° to 60° F. using colder chilled water to arrest the growth until it is further processed.

TABLE 1

GROWTH MEDIUM COMPOSITION FOR CATALASE POSITIVE ORGANISMS

| INGREDIENT | PERCENTAGE | TYPICAL RANGE | PREFERRED RANGE |
|---|---|---|---|
| Dextrose | 4.0 | 2.5 to 10 | 3 to 7 |
| Yeast Extract | 2.0 | 0.5 to 5.0 | 1.5 to 4 |
| Bentonite | 2.0 | 1 to 5.0 | 1.5 to 3.0 |
| Rice Flour | 2.0 | 1.5 to 5.0 | 2 to 4 |
| Calcium Carbonate | 1.75 | 0.25 to 4.0 | 0.5 to 2.5 |
| Guar Gum | 0.25 | 0.1 to 0.50 | 0.2 to 0.3 |
| Water | 88.0 | 70.5 to 94.15 | 79.2 to 91.3 |

Procedure for preparing catalase negative organisms

The aforementioned, catalase negative, beneficial, non-pathogenic micro-organisms are transferred three times, in sterile tryptic soy broth, prior to inoculating a bulk medium. The composition of bulk medium for growing the catalase negative organisms is presented in Table 2.

TABLE 2

GROWTH MEDIUM COMPOSITION FOR CATALASE NEGATIVE ORGANISMS:

| INGREDIENT | PERCENTAGE | TYPICAL RANGE | PREFERRED RANGE |
|---|---|---|---|
| Dextrose | 5.0 | 2.5 to 10 | 3 to 7 |
| Yeast Extract | 2.0 | 0.5 to 5.0 | 1 to 3 |
| Sweet Whey Powder | 5.0 | 3.0 to 10 | 4 to 6 |
| Water | 88.0 | 94 to 75 | 92 to 84 |

The medium is reconstituted at 12.0% solids level using clean potable water. The initial pH of the medium is adjusted to 6.5 and heat treated to 170° F. to 212° F. After being held at that temperature for a period of 1 minute to 1 hour, the heat treated medium is cooled to 75° to 115° F. by recirculating cold water. The medium is inoculated with previously transferred active culture(s). The incubation is continued until the pH comes down to 4.5 to 5.5. At this stage, the medium is neutralized to 6.5 using a neutralizing means, for example, ammonium hydroxide or magnesium hydroxide. Once again, the culture is allowed to come down to pH 4.5 to 5.5. The neutralization is continued until the pH of the bulk medium can no longer change, indicating the nutrients are exhausted. At this stage, the culture is cooled to arrest further metabolism. Whenever the culture requires oxygen for growth, a sufficient amount of sterile air is purged into the fermenter to enhance the growth. Some weaker cultures could not drop the pH level down to 5.75. In those unusual circumstances, it is not necessary to neutralize the medium.

Procedure for preparing compost type culture

It is not necessary to identify each strain employed in micro-prep. Natural, commonly occurring, mixed compost organisms can be used by employing the following procedures:

A compost is prepared under controlled conditions. At the end of the compost preparation, a one pound sample is collected, placed in a sealed container, and frozen by dipping in liquid nitrogen or frozen in an ordinary freezer (−10° to −20° C.). This procedure is undertaken to destroy any live larvae or worms. The frozen compost is reconstituted in 2.5 liters of sterile broth, which is made of 5% glucose and 2.5% autolyzed yeast extract. Then the pH of the mix is adjusted to 7.0 and the mix is incubated for 12 hours. After preliminary incubation, the pH is adjusted with acid to 4.75 to 5.0 and the mix is incubated for an additional 12 hours. After 24 hours incubation, sodium chloride is added to the mix to arrive at a final concentration of 2% to 3%. Then the preparation is incubated for an additional 12 hours. This procedure is adopted to inactivate pathogenic micro-organisms.

A culture thus prepared is plated to reconfirm there are no pathogens, before being used to inoculate sterile liquid bulk medium of the same composition described for catalase positive organisms. The compost will have a mixed culture composed of both the catalase positive and catalase negative organisms. The procedure of growing the organisms is as described above for catalase positive organisms.

Alternative procedure for preparing compost type culture

A compost culture can also be prepared by using the following procedure:

Clean compost is prepared using the conventional procedure. After composting is completed, the dried compost is added to 100 gallons of water at the rate of 50 to 100 pounds. For each 100 gallons, 5 pounds of glucose and 2.5 pounds of yeast extract or any suitable stimulant is added. The pH of the compost is adjusted to 7.0 to 7.5 and incubated at room temperature for 24 hours. At the end of the incubation, the pH is adjusted to 4.75 by addition of suitable acid or acid salt and sodium chloride, to arrive at 2% to 3% final salt concentration. The liquid culture is further incubated for 24 hours. At the end of the incubation, pH is adjusted to 7.0 to 7.5 using a basic neutralizer, such as sodium hydroxide, and the contents are filtered to produce a culture free of debris. Optionally, a yeast and mold inhibitor, such as sodium propionate, is added to arrest growth of yeast and mold. The culture can be further diluted to adjust the cell numbers. This procedure of growing at low pH and adding salt further assures that the compost culture is free from pathogenic micro-organisms. Every batch is checked for the absence of pathogenic micro-organisms. The culture thus prepared can be held at room temperature or cooled to 40° F. to slow the growth of micro-organisms.

PREPARATION OF MICRO-PREP

Organisms prepared according to the described procedures are mixed together in desired ratios depending upon the application. The liquid mixed culture is then dried to make micro-prep, using the following procedure:

For every 100 pounds of liquid culture, the ingredients listed in Table 3 are mixed in a mixer until a doughy mass is obtained. After the mass reaches the specified consistency, the mass is extruded to form wet pellets. The wet pellets are dried under sanitary conditions using a drier at ambient temperature. The culture also can be pelletized or shaped to any size or dimension, depending on the application. Optionally, enzymes can be included in the body of the pellets or sprayed on to the pellets after they are extruded. For example: protease enzyme can be included in the body of the micro-prep, and catalase enzyme can be sprayed on to the surface of the pellet.

TABLE 3

COMPOSITION OF MICRO-PREP

| INGREDIENT | PERCENTAGE[a] | TYPICAL RANGE | PREFERRED RANGE |
| --- | --- | --- | --- |
| Lecithin | 1.50 | 0.25 to 5.00 | 1.00 to 3.00 |
| Sodium Propionate | 0.15 | 0.05 to 0.30 | 0.10 to 0.20 |
| Potassium Sorbate | 0.10 | 0.05 to 0.30 | 0.05 to 0.15 |
| Guar Gum | 1.00 | 0.25 to 2.00 | 0.50 to 1.50 |
| Calcium Carbonate | 2.25 | 0.50 to 5.00 | 1.00 to 3.00 |
| Clumping Bentonite | 23.00 | 7.50 to 40.00 | 10.00 to 30.00 |
| Vegetable Flour | 65.00 | 30.00 to 80.00 | 40.00 to 70.00 |
| Catalase Enzyme | 1.00 | 0.10 to 10.00 | 0.50 to 2.50 |
| Protease Enzyme | 1.00 | 0.10 to 10.00 | 0.50 to 2.50 |
| Cellulase enzyme | 1.00 | 0.10 to 10.00 | 0.50 to 2.50 |
| Amylase Enzyme | 1.00 | 0.10 to 10.00 | 0.50 to 2.50 |
| Pectinase Enzyme | 0.10 | 0.05 to 5.00 | 0.075 to 1.00 |
| Lipase Enzyme | 0.50 | 0.05 to 5.00 | 0.10 to 1.50 |
| Sodium Bicarbonate | 2.00 | 0.25 to 5.00 | 0.20 to 3.00 |
| Glucose Oxidase | 0.25 | 0.05 to 5.00 | 0.10 to 1.50 |
| Lactase | 0.15 | 0.05 to 5.00 | 0.10 to 1.50 |

Catalase positive organisms, catalase negative organisms, mixed compost and soil organisms can be separately extruded, pelletized, and dried. Thereafter, the different pellets can be mixed in any desired proportion. For uses such as adding to a stream of water, a liquid medium may be preferred. In that case, the liquid culture micro-prep can be used directly, without pelletizing, in the form of single catalase positive or catalase negative cultures or in combination of both catalase positive and catalase negative cultures. The amount and type of liquid culture can be varied according to the desired use and application. Optionally, liquid cultures can be impregnated with enzymes, as listed in Table 4.

In another use, the liquid culture can be sprayed onto feeds as a nutritional supplement. Typical feeds include extruded, sinkable shrimp feed pellets, extruded or pelletized, floating trout or other fish feed, and dairy, poultry, piggery or other animal feed. When the micro-prep is used as a feed supplement, it can be fortified by nutrients such as vitamins, minerals, amino acids, fatty acids, non-specific stimulatory compounds, proteins, lipids and phospholipids. Thus, the micro-prep serves dual functions as a probiotic bacterial culture and also as a beneficial supplement.

The dried micro-prep is stable at room temperature and can be utilized by a variety of techniques. As an addition to feeds, the micro-prep can be pulverized. For use in ponds or wetlands, it can be sunk in water. It is stable under water for a period of 30 minutes to 5 hours. Stability in water is increased or decreased by altering the amount of binders and hydrocolloids in the preparation. The ability to sink micro-prep is important to its use as a bottom feeding marine feed, such as for shrimp or some fish. The sinkability also is important when the micro-prep is used to treat polluted waters at the bottom of ponds. The dried micro-prep releases bacteria, substrates, and enzymes over a substantial period of time into the surrounding water. It is locally effective even in large bodies of water, allowing treatment that previously was not possible.

COMPOSITION AND PREPARATION OF OXY-PREP

The oxy-prep is composed of oxygen-containing ingredients in a stable condition, such that oxygen is released upon stimulation from the micro-prep. A peroxide such as hydrogen peroxide serves as a source compound for release of oxygen. Urea combines with hydrogen peroxide to form carbamamide peroxide, a powder that is stable when dry. However, if dry carbamamide peroxide powder is mixed with water, it solubilizes almost immediately and releases the hydrogen peroxide into the water, where the hydrogen peroxide can become destabilized and release its oxygen quite easily. In oxy-prep the carbamamide peroxide is stabilized so that it releases oxygen more slowly and primarily in the presence of a destabilizing means. Lecithin serves as a suspending agent and emulsifier. Gum is a hydrocolloid that forms a matrix and modulates the rate of oxygen release. Flour is used to produce a doughy mixture that can be shaped, molded or pelletized and also adds nutrient value. Washed silica adds density without destabilizing the oxygen from the carbamamide peroxide or other source compound. A preferred composition is a combination of the ingredients listed in Table 4.

TABLE 4

COMPOSITION OF OXY-PREP

| INGREDIENT | PERCENTAGE | TYPICAL RANGE | PREFERRED RANGE |
| --- | --- | --- | --- |
| Hydrogen Peroxide (35%–75% strength) | 15.00 | 2.5 to 40 | 15 to 30 |
| Urea | 15.00 | 5 to 40 | 10 to 50 |
| Lecithin | 1.25 | 0.1 to 5.0 | 1.0 to 3.0 |
| Guar Gum | 0.75 | 0.5 to 4.0 | 0.60 to 2.5 |
| Silica | 23.00 | 10 to 60 | 20 to 40 |
| Rice Flour | 45.00 | 20 to 80 | 40 to 60 |

These ingredients are combined and mixed together until they form a fairly uniform doughy mass. This mass is extruded into pellets or molded into different shapes (squares, round balls, etc.). The extruded or molded mass is dried in a drier at an ambient temperature. The dried oxy-prep can be stored at room temperature for an extended period, such as one or more years without losing the activity.

The composition of oxy-prep is modifiable by variations and substitutions in the listed ingredients. Among the possible substitutions, hydrogen peroxide can be replaced with a different substance capable of liberating oxygen upon contact with water. Proteinaceous compounds such as yeast proteins, whey protein concentrates, caseinates, vegetable proteins, nonfat dry milk, or the like, may replace urea. Such proteinaceous compounds appear to stabilize the oxygen liberating compound during drying and subsequent storage. Silica can be replaced with bentonite, such as sodium or calcium bentonite and especially the clumping types of bentonite, although storage stability is notably reduced. For purposes of stabilizing the oxy-prep for long term storage, washed, metal free silica is preferred. Enzymes are an optional addition to the oxy-prep composition, which can be included as long as they are of the type that do not have peroxide destabilizing properties. Catalase enzyme will liberate oxygen by reacting with oxygen yielding peroxides. However, catalase can be used without harming the oxy-prep, provided that it is dried before it is applied to the dried oxy-prep. Further, dried, finely powdered micro-prep can be adsorbed onto oxy-prep. Rice flour can be replaced by any other vegetable flour, such as corn, potato, or the like, provided the replacements are free of enzymes that destabilize oxygen bearing compounds such as hydrogen peroxide.

The oxy-prep has a number of characteristics that make it both useful and unique in its ability to treat polluted bottom waters. Initially, oxy-prep is stable over a long period of time, which enables it to be manufactured, shipped, stored, and used on a practical basis. In use, it is sinkable, so that it reaches the local area that requires treatment. When treating large bodies of water, the ability to apply the treatment in a localized area is important. The oxy-prep treats water by releasing oxygen gradually, which allows the oxygen to be absorbed efficiently into the local water, rather than being lost by a rapid bubble discharge. The oxygen is released due to the interaction of oxy-prep with the enzyme, catalase. The release mechanism is both effective and specific. When catalase enzyme is not present, oxy-prep does not release oxygen despite exposure to water for more than 24 hours. Even after oxy-prep is exposed to water for 24 hours, the addition of a small amount of catalase initiates oxygen release. When hydrogen peroxide is the oxygen releasing agent in oxy-prep, the peroxide fraction is immobilized or stabilized and tends to stick with the pellet, rather than leaching quickly into water. The oxy-prep pellet is non-toxic to the aquatic or marine animals, such as shrimp and fish. In addition, the pellet is non-corrosive and non-toxic to humans and other animals. Thus, oxy-prep is uniquely suited to generate nascent oxygen in localized zones, at a water-absorbable rate, over a substantial time period, to effectively destroy anaerobic, pollution creating bacteria. At the same time, the oxy-prep maintains high levels of dissolved oxygen in the water, which reduces pollution and supports growth of aquatic or marine animals. The ability to optionally include non-reactive nutrients and vitamins further increases the potential benefits of this product. The oxy-prep works in cooperation with the micro-prep, which supplies the enzyme, catalase, to stimulate production of oxygen. The amount and strength of micro-prep controls catalase production, in turn controlling the amount and speed of oxygen production. Further, dried oxy-prep can be applied in ponds and other environments without any special equipment. The pellets are easily handled and can be thrown by hand or spread with many known types of dumping or broadcasting equipment.

Oxy-prep and micro-prep can be handled and used in many different ways. They may be included into shrimp and fish feeds at the rate of 0.01 to 20.0% by weight. Also, the ratios of oxy-prep and micro-prep can be altered depending upon the circumstances. For example, more oxy-prep should be used with feed during night time feeding. Conversely, less oxy-prep should be used during mid-day for reduced oxygen production. They can be placed in separate small bags and thus can be included into packaged shrimp or fish feed. Oxy-prep alone can be placed in a non-pervious bag, while micro-prep can be mixed with feed. Generally, it is preferable to keep the two preparations separate from each other during storage, especially if moisture is present. However, under dry conditions, they can be mixed together without adverse effect. For example, it is acceptable to dust powdered micro-prep onto oxy-prep as long as the micro-prep is sufficiently dry and free from moisture that no reaction occurs during storage.

Shapes, sizes, weights and meshes of micro-prep and oxy-prep are adjusted according to the purpose. The oxy-prep and micro-prep can be extruded in any shape, size and weight. For use in ponds to reduce pollution, foul odors, COD (chemical oxygen demand), BOD (biochemical oxygen demand), suspended solids and hydrocarbons, the preparations can be applied directly or included in shrimp feed. For the latter purpose, they are extruded into the same shape and size as the feed or made bigger to prevent their being eaten right away. For use in fish feed, they are extruded to be either larger or much smaller than the feed, so that fish do not eat them before they generate oxygen. If desired, they can be lowered to the bottom of ponds in bags, cages, or other protective housing means that prevent their being eaten by aquatic animals. For use in animal feeds, they are pulverized. For use in fertilizer applications, they are molded, pulverized or extruded, according to the application. For use as an additive to raw milk, the food grade oxy-prep and micro-prep are prepared either as powders or liquids. The liquids may be used in frozen state.

The following examples further illustrate the composition, utility, and method of preparing the invention:

EXAMPLE 1

Cultures having catalase enzyme and peroxides are applied to reduce COD, BOD, odor and color of food plant lagoon water. The catalase positive organisms and catalase negative organisms listed under Composition of Micro-Prep were prepared, using respective procedures for preparing catalase positive and catalase negative organisms, as noted above. The catalase positive cultures were divided into two fractions. To one fraction, additional catalase enzyme, 0.1 to 2.0%, (preferably 1.0%) was added. Both the fractions were dried using the Preparation of Micro-Prep procedure, above. Similarly, the catalase negative cultures were divided into two fractions. To one fraction, carbamamide peroxide (hydrogen peroxide mixed with urea) was added. Both fractions were dried using the Preparation of Micro-Prep procedure, above. All of the above four preparations will be termed "cultures" or "cultured." Similar preparations without using bacterial cultures will be termed, "controls." All four controls had the basic sterile bacterial medium without any cultures. The cultures and controls were numbered as follows:

1. Cultured catalase positive micro-organisms only (Culture-1).
2. Cultured catalase positive micro-organisms plus added catalase enzyme (Culture-2).
3. Cultured catalase negative micro-organisms only (Culture-3).
4. Cultured catalase negative micro-organisms and carbamamide peroxide (Culture-4).
5. Control sterile medium only (Control-5).
6. Control sterile medium and added catalase enzyme (Control-6).
7. Control sterile medium only (Control-7).
8. Control sterile medium and carbamamide peroxide (Control-8).

A composite sample of lagoon water was dispensed into several one liter bottles. The lagoon water without any cultured or non-cultured preparation served as a negative control. Various combinations of cultured and non-cultured preparations were inoculated at a final concentration of 0.5% into 1 liter bottles and incubated at room temperature for a period of 4 weeks. The lagoon samples were analyzed for COD, BOD odor and color at three points: at the start, prior to inoculation; at 2 weeks; and at 4 weeks of incubation. The results of this experiment are presented in Table 5.

TABLE 5

| VARIABLE | BOD Start | BOD 2 Weeks | BOD 4 Weeks | COD Start | COD 2 Weeks | COD 4 Weeks | ODOR[a] Start | ODOR[a] 2 Weeks | ODOR[a] 4 Weeks | COLOR[b] Start | COLOR[b] 2 Weeks | COLOR[b] 4 Weeks |
|---|---|---|---|---|---|---|---|---|---|---|---|---|
| Negative Control[c] | 458 | 422 | 403 | 1210 | 1155 | 1022 | +++++ | ++++ | ++++ | +++ | +++ | +++ |
| Culture 1 | 458 | 252 | 200 | 1210 | 455 | 300 | +++++ | +++ | ++ | +++ | ++ | ++ |
| Culture 2 | 458 | 261 | 198 | 1210 | 443 | 293 | +++++ | +++ | ++ | +++ | ++ | ++ |
| Culture 3 | 458 | 220 | 190 | 1210 | 420 | 320 | +++++ | +++ | ++ | +++ | ++ | ++ |
| Culture 4 | 458 | 210 | 210 | 1210 | 520 | 365 | +++++ | ++ | + | +++ | ++ | + |
| Culture 1 & 3 | 458 | 130 | 32 | 1210 | 280 | 165 | +++++ | ++ | +/− | +++ | + | +/− |
| Culture 1 & 4 | 458 | 110 | 20 | 1210 | 230 | 126 | +++++ | + | − | +++ | + | − |
| Culture 2 & 3 | 458 | 133 | 34 | 1210 | 291 | 159 | +++++ | ++ | +/− | +++ | + | +/− |
| Culture 2 & 4 | 458 | 102 | 17 | 1210 | 218 | 116 | +++++ | + | − | +++ | + | − |
| Control 5 | 458 | 410 | 350 | 1210 | 980 | 625 | +++++ | +++ | +++ | +++ | +++ | +++ |
| Control 6 | 458 | 404 | 342 | 1210 | 978 | 807 | +++++ | +++ | +++ | +++ | +++ | +++ |
| Control 7 | 458 | 388 | 364 | 1210 | 963 | 822 | +++++ | +++ | +++ | +++ | +++ | +++ |
| Control 8 | 458 | 320 | 290 | 1210 | 725 | 650 | +++++ | +++ | ++ | +++ | ++ | ++ |
| Control 5 & 7 | 458 | 403 | 345 | 1210 | 955 | 832 | +++++ | +++ | +++ | +++ | +++ | +++ |
| Control 5 & 8 | 458 | 352 | 336 | 1210 | 658 | 592 | +++++ | +++ | ++ | +++ | ++ | + |
| Control 6 & 7 | 458 | 407 | 356 | 1210 | 943 | 845 | +++++ | +++ | +++ | +++ | +++ | +++ |
| Control 6 & 8 | 458 | 325 | 312 | 1210 | 595 | 568 | +++++ | +++ | ++ | +++ | ++ | + |
| Control 1 & 2 | 458 | 248 | 205 | 1210 | 430 | 300 | +++++ | +++ | ++ | +++ | ++ | ++ |
| Control 3 & 4 | 458 | 200 | 200 | 1210 | 480 | 350 | +++++ | +++ | ++ | +++ | ++ | + |
| Control 5 & 6 | 458 | 400 | 350 | 1210 | 980 | 800 | +++++ | +++ | +++ | +++ | +++ | +++ |
| Control 7 & 8 | 458 | 330 | 310 | 1210 | 750 | 700 | +++++ | +++ | ++ | +++ | ++ | ++ |

[a]Odor Rating: +++++ = Highly Objectionable; ++++ = Distinctly Putrid; +++ = Putrid; ++ = Mildly Putrid; + = Slight Off Odor; +/− = Not Objectionable; − = No Odor Perceived.
[b]Color Rating: +++ = Distinct Black; ++ = Slightly Black; + = Blackish Orange; +/− = Orange; − = Very Slight Orange.
[c]Negative Control = Lagoon water by itself.

The results indicate that catalase positive and peroxide producing catalase negative cultures significantly reduced BOD and COD in the lagoon water. The foul odor was drastically reduced and, at the same time, the black color was reduced to a slightly orange color. Impregnating catalase positive cultures with catalase enzyme and impregnating catalase negative cultures with hydrogen peroxide produced an immediate release of oxygen, which increased the activity of aerobic micro-organisms to digest solids. The singlet nascent oxygen may be toxic to anaerobic micro-organisms that produce foul odor compounds. The disappearance of black color may be due to oxidation of hydrogen sulfide by the action of added micro-organisms. The results confirm the ability of bacterial cultures to reduce pollution. Organic preparations such as carbamamide peroxide and enzymes also have an effect. However, the combination of organic preparations, enzymes and bacterial preparations significantly speed the reactions to reduce pollution in a relatively short span.

EXAMPLE 2

Catalase positive organisms, catalase negative organisms, and catalase enzyme were combined, dried and applied to lagoon water. Hydrogen peroxide (35% to 75%) was dried into pellets and applied.

Oxy-prep was prepared according to the procedure outlined in Composition and Preparation of Oxy-Prep, above. Micro-Prep was prepared according to the procedure outlined in Preparation of Micro-Prep, above. Dried oxy-prep and micro-prep were added at the rate of 1% each into lagoon water to determine whether, together, they could reduce the COD, BOD, odor and color. Oxy-prep and micro-prep, inoculated individually, served as controls. All three samples, along with negative controls, were incubated for a period of 4 weeks. Samples were analyzed for BOD, COD, odor and color at three points: at the start, at the end of 2 weeks, and at the end of 4 weeks. The results are presented in Table 6.

TABLE 6

| VARIABLE | BOD Start | BOD 2 Weeks | BOD 4 Weeks | COD Start | COD 2 Weeks | COD 4 Weeks | ODOR[a] Start | ODOR[a] 2 Weeks | ODOR[a] 4 Weeks | COLOR[b] Start | COLOR[b] 2 Weeks | COLOR[b] 4 Weeks |
|---|---|---|---|---|---|---|---|---|---|---|---|---|
| OXy-Prep | 520 | 370 | 290 | 1300 | 880 | 790 | +++++ | +++ | ++ | +++ | ++ | ++ |
| Micro-Prep | 520 | 160 | 45 | 1300 | 350 | 200 | +++++ | ++ | + | +++ | ++ | + |
| Oxy-Prep & Micro-Prep | 520 | 70 | 10 | 1300 | 150 | 0 | +++++ | − | − | +++ | − | − |
| Negative Control[c] | 520 | 460 | 430 | 1300 | 1210 | 1150 | +++++ | +++++ | ++++ | +++ | +++ | +++ |

[a]Odor: +++++ = Highly Objectionable; ++++ = Distinctly Putrid; +++ = Putrid; ++ = Mildly Putrid; + = Slight Off Odor; − = No Odor Perceived.
[b]Color Rating: +++ = Distinct Black; ++ = Slightly Black; + = Blackish Orange; +/− = Orange; − = Very Slight Orange.
[c]Negative Control = Lagoon water by itself.

The results show that the combination of oxy-prep and micro-prep reduce BOD, COD, odor and color of the lagoon water. As shown in Example 1, micro-prep and oxy-prep individually exhibited pollution reducing abilities. An effective micro-prep can be prepared by blending catalase positive bacteria, catalase negative bacteria, and catalase enzyme. Also, an effective dried oxy-prep can be prepared by employing dried hydrogen peroxide.

EXAMPLE 3

Enzymes such as protease, lipase, cellulase, amylase, pectinase, lactase, glucose oxidase, and galactose oxidase were applied in micro-prep for reducing suspended solids and pollution. Micro-prep was prepared with the addition of the above mentioned enzymes, according to the procedure for Preparation of Micro-Prep, above. Dried oxy-prep and micro-prep were added to shrimp pond water at the rate of 0.25% and incubated at room temperature for a period of one week. Oxygen levels were checked before and after addition of the preparations. Suspended solids were measured at 0 time, after 2 days, and after 7 days. The level of suspended solids corresponds to the level of pollution. The results are presented in Table 7.

TABLE 7

| VARIABLE | OXYGEN MEASUREMENTS OF SHRIMP POND WATER | | | SUSPENDED SOLIDS mg/liter OF SHRIMP POND WATER | | |
|---|---|---|---|---|---|---|
|  | Beginning | 1 Hour Later | 24 Hours Later | Beginning | 48 Hours Later | 1 Week Later |
| Oxy-Prep | 2.5 ppm | 6.0 ppm | 3.5 ppm | 80 | 77 | 65 |
| Micro-prep with catalase only | 2.5 ppm | 2.5 ppm | 2.0 ppm | 80 | 50 | 35 |
| Micro-Prep with catalase & all other enzymes | 2.5 ppm | 2.5 ppm | 2.0 ppm | 80 | 35 | 15 |
| Oxy-Prep & Micro-prep with catatse only | 2.5 ppm | >20 ppm | 12 ppm | 80 | 42 | 21 |
| Oxy-Prep & Micro-prep with catalase & all other enzymes | 2.5 ppm | >20 ppm | 13 ppm | 80 | 10 | 7 |
| Control | 2.5 ppm | 2.5 ppm | 1.5 ppm | 80 | 78 | 76 |

Oxygen production increased with use of oxy-prep and micro-prep in shrimp pond water. Neither micro-prep, alone, nor oxy-prep, alone, could maintain an equivalently high level of oxygen. Oxy-prep, alone, was superior to micro-prep, alone, in elevating oxygen levels. This result might be explained by the presence of natural aerobic organisms and residual enzymes in the shrimp pond water. However, micro-prep was better than oxy-prep in reducing the suspended solids content. The combination of oxy-prep and micro-prep was notably superior to either component, alone, in producing enhanced oxygen levels and reducing levels of suspended solids. An elevated oxygen level enhanced growth of aerobic organisms, which ultimately digest pollutants. The added enzymes enhanced digestion of solids in shrimp pond water.

In a further investigation, the same micro-prep, with added enzymes, and oxy-prep compositions were added to a fish tank containing live fish, with similar results. This investigation demonstrated the safety and effectiveness of incorporating enzymes into micro-prep. These products can be employed in commercial and household fish tanks to maintain oxygen levels and to reduce suspended solids, such as excess feed and wastes.

EXAMPLE 4

Micro-prep and oxy-prep are incorporated into shrimp feed and applied to reduce environmental pollution in a shrimp pond, with a resulting decrease in shrimp mortality and increase in shrimp yield, body weight, and feed conversion ratio (FCR). FCR is defined as the weight of shrimp feed needed to produce a weight unit of shrimp from that pond.

TABLE 8

| | Composition of Shrimp Feed | | |
|---|---|---|---|
| INGREDIENT | PERCENTAGE | TYPICAL RANGE | PREFERRED RANGE |
| Fish Meal | 23.5 | 15 to 45 | 25 to 40 |
| Soy Bean Meal | 32.0 | 10 to 40 | 20 to 35 |
| Corn Gluten | 15.0 | 2.5 to 22.5 | 10 to 20 |
| Wheat Flour | 17.0 | 5.0 to 30.0 | 7.5 to 20 |
| Whey Powder | 5.0 | 0.10 to 10.0 | 4 to 6 |
| Pellet Binder | 3.0 | 1.0 to 5.0 | 2 to 4 |
| Fish-Oil | 1.5 | 0.5 to 2.5 | 1 to 2 |
| Fish-multi vitamins and minerals | 0.60 | 0.2 to 1.5 | 0.5 to 0.75 |
| Lecithin | 1.35 | 0.1 to 2.5 | 0.75 to 1.75 |

TABLE 8-continued

Composition of Shrimp Feed

| INGREDIENT | PERCENTAGE | TYPICAL RANGE | PREFERRED RANGE |
|---|---|---|---|
| $CaCo_3$ | 0.25 | 0.1 to 2.0 | 0.2 to 1.5 |
| Egg Digest- (cholesterol source) | 0.25 | 0.1 to 1.0 | 0.2 to 0.6 |
| Stabilized Vit-C | 0.20 | 0.05 to 0.40 | 0.1 to 0.3 |
| Sodium Propionate | 0.20 | 0.05 to 0.40 | 0.1 to 0.3 |
| Powdered yucca-schidigera extract | 0.03 | 0.01 to 1.0 | 02 to 0.06 |
| Ethoxyguin | 0.02 | .015 to .1 | 0.01 to .05 |
| Heat stable multi-enzyme and multi-mineral mix | 0.10 | 0.05 to 0.25 | 0.075 to 0.15 |

(a): Pellet binder supplied by Martin Marietta; brand name is Pel Plus 250-A. When the feed was extruded as opposed to pelleting, the pellet binder was not used.
(b): Fish multivitamins and stabilized Vit-C was supplied by Hoffman Laroche.
(c): Yucca Schidigera extract was supplied by All-Tech, Inc.

The shrimp feed of Table 8 is nutritionally well balanced to support shrimp growth. This feed is designated "normal feed." Normal feed was modified by adding 2.5% each of oxy-prep and micro-prep at manufacture. This modified feed is designated "oxy & micro-feed." The micro-prep and oxy-prep were prepared as in prior examples, with added nutrients and supplements. Where only micro-prep was present in normal feed, the product is designated "micro-feed." Normal feed having only oxy-prep added is designated "oxy-feed." All four feeds were tested in four different ponds through harvest. Oxygen content was monitored each morning and at mid-afternoon. At harvest, mortality rates, yield, and rheological quality were evaluated. Also, the color and odor of the pond bottoms were evaluated to determine level of pollution. The results are presented in Tables 9 and 10.

TABLE 9

| VARIABLE | FCR | % Mortality | Pond Bottom Condition after harvest | Range of Oxygen Readings During Entire Growth Period | | Weight of Shrimp |
|---|---|---|---|---|---|---|
| | | | | Morning | Mid-Day | |
| Control feed | 1.8 | 22.5 | poor | 2.75–3.50 | 5.0–7.0 | average |
| Micro-feed | 1.6 | 15 | average | 3.00–3.75 | 5.5–7.5 | good - 7.0% > than control |
| Oxy-feed | 1.45 | 13 | average | 3.50–4.50 | 6.0–8.0 | 8% > than control |
| Micro & Oxy-feed | 1.2 | 2.5 | excellent | 5.50–7.00 | 7.0–9.0 | excellent - 12% > control |

TABLE 10

PHYSICAL AND RHEOLOGICAL QUALITY OF THE RAW AND COOKED SHRIMP OBTAINED USING DIFFERENT FEEDS

| | RAW SHRIMP QUALITY | | | | | |
|---|---|---|---|---|---|---|
| Variable | shell | flesh firmness | color & overall appearance | black spots on body | INTACTNESS OF RAW SHRIMP WITH | |
| | | | | | freezing | thawing |
| Control | weak & plastic | weak & slightly pasty | ++ | 8 | ++ | ++ |
| Micro-feed | slightly firm | moderately firm & not pasty | +++ | 5 | +++ | +++ |
| Oxy-feed | slighty firm | moderately frim & not pasty | +++ | 4 | +++ | +++ |
| Micro-feed & Oxy-feed | firm & springy | firm & not pasty | ++++ | 1 | ++++ | ++++ |

| | PERCENTAGE SHRINKAGE IN SHRIMP WITH DIFFERENT COOKING METHODS | | | | |
|---|---|---|---|---|---|
| Variable | boiling | microwave | stir-frying | cooking in sauce | SHRIMP COLOR AFTER BOILING |
| Control | 23 | 6.5 | 25 | 35 | pinkish |
| Micro-feed | 18 | 4 | 19 | 31 | light reddish |
| Oxy-feed | 18 | 3.5 | 18.25 | 27 | light reddish |

TABLE 10-continued

PHYSICAL AND RHEOLOGICAL QUALITY OF THE RAW AND COOKED SHRIMP
OBTAINED USING DIFFERENT FEEDS

| | | | | | |
|---|---|---|---|---|---|
| Micro-feed & Oxy-feed | 12 | 1.25 | 13 | 21 | light reddish |

The results indicate that, individually, micro-feed and oxy-feed were superior to the control, normal feed, in terms of maintaining oxygen levels both in the morning and at mid-day. The combined oxy & micro-feed exceeded the separately added micro-feed or oxy-feed in maintaining oxygen levels. In addition, it lowered the FCR ratio and mortality rate, increased shrimp weight, improved the condition of the pond bottom, and reduced black spot disease. The quality of the shrimp improved both in terms of rheological properties and reduced weight loss after cooking. Inclusion of oxy-prep and micro-prep in shrimp feed improved yield and quality of shrimp and reduced bottom pollution.

Oxy-prep and micro-prep were added to feed in amounts ranging from 1% to 20.0%. The results indicate that 1.0% to 10.0% of the oxy-prep and micro-prep improved the shrimp farming efficiency by reducing pollution. These preps, even in small quantities (<1%) made a difference in reducing pollution when incorporated into feed. Direct use in ponds, without mixing with feed, produced similar results. When applied to fish farming, the preps showed improvement in fish yield and quality, while reducing pond pollution.

EXAMPLE 5

An alkaline pH buffer is beneficial in maintaining oxygen levels in a pond. Two shrimp feeds were prepared. The first, designated as buffered regular feed, contains 1.5% sodium bentonite (sodium montmorillonite) as a buffer for maintaining pH between 7.8 and 8.75. The second, designated non-buffered regular feed, contains no bentonite or other pH buffer and is the normal feed of Table 8. Third and fourth feeds were prepared by adding oxy-prep and micro-prep to the respective buffered and non-buffered regular feeds. In both feeds employing sodium bentonite, a corresponding percentage of soy bean meal was eliminated from the formula of Table 8. All four feeds were added to different shrimp ponds and the oxygen contents were monitored. Also, at the end of the harvest, the condition of the pond bottom was examined. The results are presented in Table 11.

TABLE 11

| | OXYGEN CONTENT RANGE | | POND BOTTOM |
|---|---|---|---|
| TYPE OF FEED USED | MORNING | MID-DAY | CONDITION |
| Non-buffered feed Non-buffered feed | 2.50 to 3.25 | 5.25 to 7.0 | poor |
| Oxy-prep Micro-prep Buffered feed | 3.75 to 5.50 | 7.25 to 8.75 | excellent |
| | 3.0 to 4.25 | 5.75 to 7.5 | average |
| Buffered feed Oxy-prep Micro-prep | 5.0 to 7.0 | 8.25 to 9.75 | excellent |

Buffered feeds produced higher dissolved oxygen readings than non-buffered feeds. The buffered feed with oxy-prep and micro-prep showed significant increases in oxygen content both in the morning and at mid-afternoon, and the pond bottom condition was superior to the non-buffered regular feed. Similar experiments were conducted using 0.1% to 5.0% sodium bentonite levels in buffered feeds. The results show that even a small amount of buffering had a significant effect in enhancing oxygen levels.

Other buffers such as sodium bicarbonate (0.1 to 2.5%) were evaluated. While the other buffers also had pronounced effect on maintaining the dissolved oxygen level, sodium bentonite proved superior. A combination of various buffers also proved successful. Additional mineral buffers such as smectites, zeolite, magnasite and perlite were tested in combination with bentonite. Both zeolite and perlite were effective to improve the condition of the pond bottom, when used in feed together with bentonite and other buffers. While improving oxygen content and reducing bottom pollution, natural minerals such as bentonite, zeolite and perlite are harmless to shrimp.

The best pond bottom conditions resulted from use of sodium bentonite, followed by zeolite, and then perlite. Zeolite and perlite are desirable additions to shrimp feed, in combination with bentonite. However, the best results follow when the aquatic feed contains micro-prep and oxy-prep, in addition to the mineral additives.

EXAMPLE 6

With the increased mid-day oxygen levels of Example 5, it is probable that the concentration of algae will increase. Acid blue #9 food dye (0.5%) and/or chelated $CuSO_4$ were added to shrimp feed at a rate of 1.5 pounds per ton of feed, along with buffers to improve uniformity of oxygen levels in a pond both at night and daytime. Acid blue #9 was added to buffered shrimp feed containing both oxy-prep and micro-prep. In some samples, chelated $CuSO_4$ was included to arrive at 2 to 5 PPM in the final feed. Buffered shrimp feed containing oxy-prep and micro-prep, but with no acid blue #9, served as a control. All these preps were added to the shrimp ponds and the oxygen levels were monitored throughout the growth period. At the end of harvest, the condition of the pond bottoms were examined for pollution. The results are presented in Table 12.

TABLE 12

| | RANGE OF OXYGEN CONTENT | | CONDITION OF |
|---|---|---|---|
| FEED COMPOSITION | MORNING | MID-DAY | POND BOTTOM |
| Buffered feed | | | |
| Acid blue #9 Oxy-prep Micro-prep Buffered feed | 5.25 to 7.10 | 7.25 to 8.50 | excellent |
| Oxy-prep Micro-prep | 4.75 to 6.8 | 8.0 to 10.0 | excellent |

TABLE 12-continued

| FEED COMPOSITION | RANGE OF OXYGEN CONTENT | | CONDITION OF POND BOTTOM |
|---|---|---|---|
| | MORNING | MID-DAY | |
| Buffered feed | | | |
| Acid blue #9 | | | |
| Chelated $CuSO_4$ | 6.25 to 7.0 | 7.25 to 7.80 | excellent |
| Oxy-prep | | | |
| Micro-prep | | | |
| Buffered feed | | | |
| Chelated $CuSO_4$ | 5.10 to 6.5 | 7.7 to 9.50 | excellent |
| Oxy-prep | | | |
| Micro-prep | | | |

Oxygen levels were more uniform both in the morning and at mid-day when the shrimp feed included acid blue #9.

Acid blue #9 was added to micro-prep and then added to the feed. Oxygen levels became uniform. The experiment was repeated with acid blue #9 dye in non-buffered feed and also found improved stabilization of oxygen levels. The addition of chelated $CuSO_4$ to buffered feed also stabilized the oxygen levels, at an inclusion rate of 2.5 PPM. However, acid blue #9 food dye was superior to chelated $CuSO_4$.

The combination of acid blue #9 and chelated $CuSO_4$ produced a better result than either agent, alone. Acid blue #9 was evaluated at levels ranging from 0.1 lb/ton of feed to 3.0 lbs/ton of feed. Chelated $CuSO_4$ was tested from 0.25 PPM to 5.0 PPM in the feed. The combination of dye and chelated $CuSO_4$ was more effective to lower concentrations than possible with the individual components.

At times during the experiment, acid blue #9 or chelated $CuSO_4$ were used with shrimp feed but without oxy-prep and micro-prep. On those days, oxygen was added to the ponds by typical mechanical oxygenating means, such as pumps or paddles. Both morning and mid-day oxygen levels remained good. As a result, it appears that algae and phytoplankton are controlled by acid blue #9 or chelated $CuSO_4$ without harm to shrimp, as long as an oxygenating means or oxygen source is employed. One such oxygen source, of course, is oxy-prep, which might be used successfully by itself if the pond contains natural supplies of oxygen destabilizing substances.

EXAMPLE 7

The technology of Example 6 was modified to retard algae growth and foul odors in natural and ornamental ponds. Micro-prep was prepared with and without acid blue #9, and with and without chelated $CuSO_4$. Acid blue #9 was added to micro-prep at 2.0%. Chelated $CuSO_4$ was added to micro-prep to arrive at 5.0 ppm. Three negative controls consisted of (1) chelated copper sulfate (2) acid blue #9 and chelated $CuSO_4$, and (3) acid blue #9. The negative controls were prepared without any micro-prep or oxy-preps and were added to the ponds at the rate of 2.5 pounds each, twice a month, per acre of pond. This experiment was carried out over a period of 2 months. The results are presented in Table 13.

TABLE 13

| PREPARATION | RETARDATION OF ALGAE BY PHYSICAL OBSERVATION | ODOR REDUCTION OF POND | OVERALL APPEARANCE OF POND |
|---|---|---|---|
| Micro-prep Oxy-prep | − | +++ | ++ |
| Micro-prep Oxy-prep Chelated $CuSO_4$ Acid blue #9 | ++++ | +++ | ++++ |
| Micro-prep Oxy-prep Acid blue #9 | +++ | +++ | +++ |
| Micro-prep Oxy-prep Chelated $CuSO_4$ | +++ | +++ | +++ |
| Chelated $CuSO_4$ | + | − | + |
| Acid blue #9 | + | − | + |
| Chelated $CuSO_4$ Acid blue #9 | ++ | − | ++ |
| None | − | − | − |

− = No improvement
+ = Insignificant improvement
++ = Slight improvement
+++ = Better improvement
++++ = Great improvement The combination of micro-prep, oxy-prep, chelated $CuSO_4$ and acid blue #9 produced the best result. This combination produced the greatest inhibition of algae and also retarded foul odors in the pond. The combination of micro-prep and oxy-prep, without chelated $CuSO_4$ or acid blue #9, was not effective to reduce the growth of algae. The combination of micro-prep, oxy prep, and either chelated $CuSO_4$ or acid blue #9 was effective to retard algae. However, a combination of all four ingredients significantly reduced algae even when small doses were used. Chelated copper sulfate, alone, or acid blue #9, alone, when used in tested doses was only slightly effective. Thus, algae retardants added to micro-prep and oxy-prep were effective to reduce the algae problem in natural and artificial ponds.

Rotofer and algicidal bacteria were combined with micro-prep and acid blue #9 to successfully retard algae. From such results, it appears that other safe and suitable algicidal compounds can also be included in micro-prep and oxy-prep, provided they are not detrimental to the functionality of the preparations.

If the use of chemicals such as $CuSO_4$, permanganate, or the like are environmentally objectionable, acid blue #9 remains a safe food dye that is effective for use in combination with micro-prep and oxy-prep to retard algae and foul odors in ponds. Small, sublethal amounts of safe food dye and chelated chemicals were effective to retard algae without polluting the ponds with objectionable chemicals. The same combinations were found successful to retard algae in swimming pools and hot tubs.

EXAMPLE 8

Food grade oxy-prep and micro-prep were applied to raw milk to retard spoilage due to the growth of bacteria, when these products are incubated in the milk either at refrigeration temperature or at room temperature. A combination of beneficial bacterial cultures, immobilized or stabilized hydrogen peroxide or hydrogen peroxide yielding enzyme substrates, and substrates such as sodium percarbonate were effective to preserve raw milk or raw milk ingredients. The enzyme substrates included glucose oxidase-glucose and galactose oxidase-galactose. Low concentrations of oxy-prep and micro-prep increase the shelf life of raw milk by activating the lactoperoxidase system, without requiring high concentrations of bacterial cultures or hydrogen peroxide.

Micro-prep was prepared following the procedure described in Preparation of Micro-Prep, above. The following food grade cultures were included in the micro-prep: *Lactococcus lactis* var. *lactis, Lactococcus lactis* var *cremoris, Lactococcus lactis* var *lactis* subspecies *diacetylactis, Lactobacillus lactis, Lactobacillus bulgaricus, Lactobacillus acidophilus, Lactobacillus helveticus* and *Streptococcus thermophilous*. The cultures were blended, and for every 100 pounds of liquid culture, the following sterile ingredients were added and extruded into pellets: lecithin 1.5 pounds, sodium propionate 0.2 pounds, calcium carbonate 2.25 pounds, guar gum 1 pound, nonfat dry milk 23 pounds, lactoperoxidase enzyme 0.1 pounds, glucose oxidase enzyme 10.0 pounds, lactase enzyme 0.1 pound, fine mesh sodium caseinate and/or vegetable flour 50 pounds. The extruded culture was dried at ambient temperature under sterile conditions. The dried culture was milled and mixed with same mesh sodium bicarbonate and glucose at a ratio of 50:50. In this preparation, catalase does not have to be added because raw milk contains trace amounts of this enzyme.

The oxy-prep was prepared by mixing 20 pounds of food grade hydrogen peroxide with 20 pounds of nonfat dry milk, 20 pounds of glucose, 10 pounds of dried casein and 1.5 pounds of liquid lecithin. In some samples, food grade urea and vegetable flour were used in the place of casein or nonfat dry milk, to tie up the hydrogen peroxide. Food grade urea functioned as effectively as high protein casein or nonfat dry milk. After the ingredients were mixed, they were extruded into pellets and dried at ambient temperature. The pellets were milled and mixed with same mesh sodium bicarbonate in a 50:50 ratio.

The micro-prep and oxy-prep powders, thus prepared, were blended in a 50:50 ratio and then added to 200 ml samples of raw milk. One group of milk samples was inoculated with oxy-prep and micro-prep at a rate equivalent to 2 grams per 100 pounds of raw milk. Another group of samples was inoculated with oxy-prep, alone, at a concentration equivalent to 2 grams/100 pounds of milk. Another group of samples was inoculated with micro-prep, alone, at a concentration equivalent to 2 grams/100 pounds of milk. An untreated sample served as control. All samples were incubated at refrigeration temperature, 4° C., for a period of 1 to 10 days. Several variations in the concentration and ratios of oxy-prep and micro-prep also were tested. The results are tabulated in Table 14.

TABLE 14

EFFECT OF MICRO-PREP & OXY-PREP ON pH, TITRATABLE ACIDITY AND ORGANOLEPTIC PROPERTIES OF RAW MILK INCUBATED AT 4° C.

| No. | Variable | Quantity of micro-prep and/or oxy-prep added to 100 lbs raw milk | pH, (Titratable Acidity), and Organoleptic Analysis | | | |
|---|---|---|---|---|---|---|
| | | | 0 time | 1 day | 2 days | 8 days |
| 1 | Raw milk | none | 6.68 (0.14) | 6.50 (0.17) | 6.45 (0.18) | 5.53 (0.44) distinct putrid smell |
| 2 | Raw milk micro-prep | 2 grams | 6.68 (0.14) | 6.66 (0.14) | 6.60 (0.15) | 5.73 (0.39) mild acid and very mild putrid smell |
| 3 | Raw milk Oxy-prep | 2 grams | 6.68 (0.14) | 6.67 (0.14) | 6.67 (0.14) | 5.75 (0.36) mild acid and very mild putrid smell |
| 4 | Raw milk Micro-prep | 1 gram micro-prep 1 gram oxy-prep | 6.68 (0.14) | 6.68 (0.14) | 6.66 (0.14) | 6.44 (0.17) fresh raw milk smell |
| 5 | Oxy-Prep | 0.5 gram micro-prep 0.5 gram oxy-prep | 6.68 (0.14) | 6.689 (0.14) | 6.64 (0.14) | 64.0 (0.18) fresh raw milk smell |
| 6 | | 0.75 gram micro-prep 0.25 gram oxy-prep | 6.68 (0.14) | 6.68 (0.14) | 6.65 (0.14) | 6.42 (0.17) fresh raw milk smell |
| 7 | | 0.25 gram micro-prep 0.75 gram oxy-prep | 6.68 (0.14) | 6.68 (0.14) | 6.68 (0.14) | 6.37 (0.18) fresh raw milk smell |

The results show that micro-prep and oxy-prep, incubated separately in raw milk, exhibited slight inhibition of spoilage bacteria, as evidenced by comparison of pH with the control. The combination of oxy-prep and micro-prep significantly inhibited spoilage bacteria over a period of 8 days. A similar result was found even with a concentration of oxy-prep and micro-prep of 100 grams/100,000 pounds of raw milk. Similar favorable results were achieved when raw milk was incubated at room temperature with the combination of micro-prep, made with lactose and proteinase negative mutants, plus oxy-prep. The results are tabulated in Table 15.

TABLE 15 pH AND ORGANOLEPTIC ANALYSIS OF RAW MILK WITH MICRO-PREP AND OXY-PREP

| No. | Variable | Quantity of micro-prep and/or oxy-prep added to 100 lbs of raw milk | pH & organoleptic analysis of raw milk incubated at room temperature | | |
|---|---|---|---|---|---|
| | | | 0 time | 1 Day | 2 Days |
| 1 | Raw milk | none | pH 6.68<br>smell - fresh raw milk | pH 627<br>smell - slight putrid | pH 5.72<br>smell - distinct putrid |
| 2 | Raw milk<br>Micro-prep | 1 gram | pH 6.68<br>smell - fresh raw milk | pH 6A8<br>smell - fresh raw milk | pH 6.05<br>raw milk smell<br>very mild off-flavor |
| 3 | Raw milk<br>Oxy-prep | 1 gram | pH 6.68<br>smell - fresh raw milk | pH 6.52<br>smell - fresh raw milk | pH 6.58<br>raw milk smell<br>slight of flavor |
| 4 | Raw milk<br>Micro-prep<br>Oxy-prep | 1 gram of micro-prep<br>1 gram of oxy-prep | pH 6.68<br>smell - fresh raw milk | pH 6.68<br>smell - fresh raw milk | pH 6.58<br>smell - fresh raw milk |
| 5 | Raw milk<br>Micro-prep<br>Oxy-prep | 0.5 grams of micro-prep<br>0.5 grams of oxy-prep | pH 6.68<br>smell - fresh raw milk | pH 6.65<br>smell - fresh raw milk | pH 6.52<br>smell - raw milk |
| 6 | Raw milk<br>Micro-prep<br>Oxy-prep | 0.75 grams of micro-prep<br>0.25 grams of oxy-prep | pH 6.68<br>smell - fresh raw milk | pH 6.68<br>smell - fresh raw milk | pH 6.53<br>smell - raw milk |
| 7 | Raw milk<br>Micro-prep<br>Oxy-prep | 0.25 grams of micro-prep<br>0.75 grams of oxy-prep | pH 6.68<br>smell - fresh raw milk | pH 6.68<br>smell - fresh raw milk | pH 6.49<br>smell - raw milk |

Organoleptic analyses revealed no abnormal flavor in the raw milk inoculated with oxy-prep and micro-prep. No residual hydrogen peroxide was detected at the end of the incubation. Thus, it appears that the known practices of adding hydrogen peroxide or beneficial bacteria are not the best means of preserving the raw milk. The use of a combination of oxy-prep and micro-prep appears to be a superior commercial technique for reducing spoilage of raw and refrigerated milk. This discovery offers significant economic savings, reduces spoilage of valuable food products, and has public health significance by reducing diseases related to consumption of spoiled food.

Similar results are obtained when hydrogen peroxide is replaced by other oxygen yielding compounds, or urea is replaced by other high protein compounds such as whole cell yeast, isolated yeast protein, vegetable protein, or milk derived proteins such as nonfat dry milk, whey protein concentrate, casein or casein hydrolyzate, provided they are free from traces of catalase or peroxide cleaving enzymes.

Further experiments evaluated a modified micro-prep to which lactose or proteinase negative mutants were added. The lactose negative mutants were induced by growing the organisms at elevated temperature, or by growing in the presence of safe mutagen, or by heat treating the culture after growth, i.e.: by heating to 100° to 165° F., preferably 145° F. for 16 sec to 30 minutes, or by adapting all procedures. The altered cultures were made into the modified micro-prep and used along with oxy-prep to retard the growth of spoilage organisms.

Milk was inoculated with the modified micro-prep and oxy-prep and was used to manufacture cheese. The slowness in the vat was minimal, indicating that bacteriophage problems were reduced. This result could be due to adsorption of bacteriophage from the raw milk to the mutants, whereby the bacteriophage was not able to multiply in the raw milk.

Oxy-prep and modified micro-prep were used to preserve milk that had to be transported without refrigeration, and the lactose and/or proteinase negative mutants listed earlier were employed. It was found that the lactose negative and/or proteinase negative mutants cannot break lactose sugar and, thus, cannot produce too much acid, even in the raw milk. The lactose negative and/or protease negative mutants prepared and made into the modified micro-prep cannot produce acid from lactose sugars or proteolyze casein. However they retained the ability to produce hydrogen peroxide to stimulate the lactoperoxidase system.

The mutants functioned equivalently when incorporated into a frozen or lyophilized micro-prep and used in raw milk. In the dairy industry, it is customary practice to use frozen liquid cultures or freeze dried preparation to inoculate milk. Accordingly, a procedure was developed to freeze oxy-prep and micro-prep together, in an oxy-micro-preparation, without damaging the bacteria. Since the hydrogen peroxide or stabilized hydrogen peroxide reacts with catalase instantly, this procedure employs a hydrogen peroxide generating substrate-enzyme combination for use in the mixed, frozen oxy-micro-preparation.

The following procedure was used to prepare the frozen oxy-micro-preparation: High hydrogen peroxide producing strains of *Lactococcus lactis* var *lactis, Lactococcus lactis* var *cremoris,* lactose and protein negative mutants of strains of *Lactococcus lactis* var. *lactis* and Lactococcus var. *cremoris* were grown using the growth medium and procedures described under Procedure for preparing catalase negative organisms, above. After the cultures were fully grown, they were blended, and for every 100 pounds of liquid culture, 20 pounds of glucose (10 to 60 pound range) was added and stirred until it went into solution. The culture was cooled immediately to 40° F. (30° to 40° F. range). After the culture was cooled sufficiently, the following enzymes were added: 20 pounds of glucose-oxidase (0.50–40 pounds range); 0.25 lbs. lactoperoxidase (0.1 to 10 lbs. range); and 1.5 lbs. lactase (0.1 to 20 lbs. range). The pH of the medium was then adjusted to 6.2 to 6.4 (5.8 to 7.0 range) and dispensed into metallic or plastic containers and were frozen immediately in liquid nitrogen or any other suitable cryogenic agent. Alternatively, the culture was dispensed in the form of beadlets into liquid nitrogen, to achieve individual quick frozen beadlets, for the convenience of dispensing into milk without thawing the culture. Such a frozen culture or beadlets can be stored frozen, such as at −40° C. for an extended period.

A dried oxy-micro-preparation was prepared by using the following procedure: the culture was prepared as described for frozen preparation. After the cultures were fully grown, they were blended, and for every 100 pounds of liquid cultures, 20 pounds of lactose (10 to 30 pounds range), 20 pounds of sodium citrate (10 to 30 lbs. range), 30 pounds of nonfat dry milk (10 to 40 pounds range), 5 pounds of cellulose (2.5 to 10 pounds range), and 2.5 pounds of silicon dioxide (1.0 to 7.5 pounds range) were added and thoroughly mixed until the mixture became a doughy mass. The mixture was molded or extruded and then dried at the ambient temperature. Prior to extrusion, an anti-molding compound such as natamycin (primaricin) was included at the rate of 2.5 to 25 grams/100 pounds. The dried culture was milled to a powdery consistency. This portion of the product constitutes the micro-prep.

Separately, 15 pounds of dried, stabilized glucose oxidase (5 to 20 pounds range), 0.25 pounds dried lactoperoxidase (0.10 to 5.0 pounds range), 1 lb. dried lactase (0.10 to 5 lb. range), 20 pounds of glucose (10 to 40 pound range) and 20 pounds of sodium bicarbonate (10 to 40 lb. range) and, optionally, 30 pounds of sodium percarbonate (5 to 50 pounds range) were mixed. The sodium percarbonate is used to speed up the reaction but is not necessary. This portion of the product constitutes the oxy-prep.

The dried micro-prep and oxy-prep were blended and appropriate amounts, such as 0.001 to 0.5 percent by weight, were added to raw milk to achieve a reduction in the growth of the spoilage organisms. The frozen oxy-micro-preparation or the dried preparation, when added to the raw milk, generate micro-quantities of hydrogen peroxide. This hydrogen peroxide activates the lactoperoxidase system, in turn reducing the growth of milk spoilage organisms. As a result, the life of raw milk is extended, whether the milk is stored in milk cans or silos.

The shelf life of the fresh fruit juice was extended by adding small quantities of oxy-micro-preparation, along with sodium or potassium thiocyanate and lactoperoxidase enzyme. No change in the color, flavor or taste was observed. Similar results were obtained with fresh salads, pickles, fresh cut vegetables, shrimp, meat, fish and brine tanks. The use of oxy-prep and micro-prep is broad-based in food preservation applications.

EXAMPLE 9

This example demonstrates the effectiveness of micro-prep and oxy-prep in reducing hydrocarbons and petroleum smells. Micro-prep was prepared with strains of genus Pseudomonas, *Bacillus subtilus* and non-specific, non-pathogenic unidentified spherical and rod shaped bacteria isolated from soils impregnated with petroleum, diesel, or other hydrocarbons, and from farm and dairy compost. The procedure for making the culture from compost or natural sources is described above. The resulting dried culture was designated as micro-prep. Hydrogen peroxide and urea were mixed separately with vegetable flour, filler, and/or bentonite compounds, and this dried preparation was designated as oxy-prep.

Hydrocarbon contaminated water was dispensed into 4 erlenmeyer flasks. Flask #1 was inoculated with 1% of micro-prep. Flask #2 was inoculated with 1% oxy-prep. Flask #3 was inoculated with 0.5% each of micro-prep and oxy-prep. Flask #4 served as a negative control. All four flasks were capped with breathable cotton plugs and were incubated at room temperature for a period of 8 weeks. At the end of the incubation period, flask were smelled and observed for physical appearance. The results are presented in Table 16.

TABLE 16

| TYPE OF PREPARATION ADDED TO HYDROCARBON IMPREGNATED WATER | SMELL OF IMPREGNATED WATER 0 TIME | HYDROCARBON END OF 8 WEEKS | PHYSICAL APPEARANCE OF IMPREGNATED WATER 0 TIME | THE HYDROCARBON END OF 8 WEEKS |
| --- | --- | --- | --- | --- |
| Micro-prep | Distinct gasoline or petroleum smell | Mild gasoline or petroleum smell | No precipitate | Slight amount of black precipitate |
| Oxy-prep | Distinct gasoline or petroleum smell | Distinct gasoline or petroleum smell | No precipitate | No precipitate |
| Micro-prep and Oxy-prep | Distinct gasoline or petroleum smell | Very faint petroleum smell | No precipitate | Large amount of black precipitate |
| None | Distinct gasoline or petroleum smell | Distinct gasoline or petroleum smell | No precipitate | No precipitate |

Storage studies were conducted on raw milk inoculated with both frozen and dried mixed oxy-micro-preparation, stored both at room temperature and at refrigeration temperature. The results were identical to the first storage experiment, indicating that both preparations can retard the growth of spoilage organisms in the raw milk. It was noted that inclusion of lactose or protein negative mutants of lactic streptococci in micro-prep, when inoculated into raw milk along with oxy-prep, eliminated the culture flavor in raw milk, even upon extended incubation.

Further experiments showed that other hydrogen peroxide generating substrate-enzyme combinations, such as galactose-galactose oxidase, can be employed to prepare the combined oxy-micro-preparation. Such other combination are effective to activate the lactoperoxidase system in raw milk or in other products where the lactoperoxidase system ingredients—lactoperoxidase and thiocyanate—are present The results show that the combination of oxy-prep and micro-prep reduced the hydrocarbon smell. The visible appearance of a black precipitate was an indication that the hydrocarbon has been cleaved. A slight amount of black precipitate resulted from use of micro-prep without oxy-prep, showing a slight effectiveness. However, the combination of micro-prep and oxy-prep produced an enhanced reaction, signifying an improved effectiveness. The combination of this micro-prep and oxy-prep appears effective to clean hydrocarbon contaminated areas.

EXAMPLE 10

This experiment determines the effectiveness of micro-prep and oxy-prep to digestion of grease and proteins in the grease traps or plumbing lines.

The micro-prep was prepared by including strains of pseudomonas, *streptococcus liquifaciens, Lactobacillus*

*salivarius*, strains of Thiobacillus, yeast and non-pathogenic mixed unidentified compost strains. After the cultures were grown, they were mixed together and the pH was adjusted to 7.5 using calcium hydroxide or sodium hydroxide. To 100 pounds of liquid culture, a vegetable flour containing 50 pounds rice flour plus 50 pounds wheat flour was then added, thickening the culture to the consistency of dough. The culture was extruded or formed into small bodies and dried quickly, thus forming the micro-prep. After it was dried, the micro-prep was grated or milled into fine mesh powder. Then, suitable powdered enzymes such as lipase, protease, amylase, cellulase and pectinase were added to the micro-prep, to arrive at 25% to 50% of the total preparation. Fifty percent of the total enzymes were made of protease and lipase.

The micro-prep thus prepared was then mixed with dry blended oxy-prep made of sodium percarbonate (4 to 8 parts), sodium bicarbonate (30 to 50 parts), sodium bi-sulfate (30 to 50 parts), metallic aluminum or aluminum salts (2 to 4 parts) and calcium carbonate (7.5 to 15.0 parts). The micro-prep and oxy-prep were mixed in five batches having ratios of 80:20, 70:30, 60:40, 50:50, 10:90. All the above mixed preparations, along with oxy-prep and micro-prep, were added to grease trap grease at 0.1% level and incubated at room temperature until the grease was digested. The results are presented in Table 17.

TABLE 17

| PREPARATION ADDED TO GREASE SAMPLES | | TIME TAKEN TO DIGEST GREASE COMPLETELY | GREASE SMELL |
|---|---|---|---|
| Micro-prep | 80% | 4 days to totally digest | Digested rancid smell |
| Oxy-prep | 20% | | |
| Micro-prep | 70% | 3 days to totally digest | Digested rancid smell |
| Oxy-prep | 30% | | |
| Micro-prep | 60% | 3 days to totally digest | Digested rancid smell |
| Oxy-prep | 40% | | |
| Micro-prep | 50% | 4 days to totally digest | Digested rancid smell |
| Oxy-prep | 50% | | |
| Micro-prep | 10% | Partial digestion observed by 7th day | Digested rancid smell |
| Oxy-prep | 90% | | |
| Micro-prep only | | 5 days to totally digest | Very slight putrid and rancid smell |

TABLE 17-continued

| PREPARATION ADDED TO GREASE SAMPLES | TIME TAKEN TO DIGEST GREASE COMPLETELY | GREASE SMELL |
|---|---|---|
| Oxy-prep only | Not digested within one week | Putrid smell |

The results show that micro-prep was able to digest the grease trap grease by about the 5th day. However, a very slight putrid smell was perceived along with the rancid smell of the grease. The addition of oxy-prep to micro-prep enhanced the grease digestion by one day and, at the same time, no putrid smell was observed. Even though the highly buffered micro-prep is capable of digesting the grease, oxy-prep is beneficial to speed-up the process.

This experiment also demonstrates that oxy-prep can produce oxygen in more than one way: A first is by contact with water, and a second is with the aid of peroxide breaking enzymes. Thus, the useful forms of oxy-prep are not limited to those containing hydrogen peroxide. For applications such as those not requiring that oxy-prep sink in water, other stable, oxygen bearing compounds can be substituted for sodium percarbonate, hydrogen peroxide, or carbamamide peroxide.

EXAMPLE 11

This experiment evaluated the utility of oxy-prep and micro-prep as additives to garden soil, to enhance the growth of tomatoes and rose bushes. Micro-prep and oxy-prep were prepared according to the procedures for preparation of micro-prep and oxy-prep, above. Four test patches, each four feet by four feet, were selected, tilled and used for the experiment. Plot 1 was used to grow tomato plants using garden fertilizer only. Plot 2 was used to grow tomato plants using commercial garden fertilizer plus 2.5% each of oxy-prep and micro-prep. Plot 3 was used to grow roses using the garden fertilizer, only. Plot 4 was used to grow roses using garden fertilizer plus 2.5% each of oxy-prep and micro-prep. All four plots were treated identically in watering and other care. The survival rate and size of the tomatoes was recorded. With the roses, the survival rate, size and number of flowers per bush were monitored. The results are reported in Table 18.

TABLE 18

| | TOMATOES | | | ROSES | | |
|---|---|---|---|---|---|---|
| FERTILIZER TYPE | Number of Tomato Plants | Number of Tomatoes | Average Weight of Tomatoes | Number of Rose Bushes | Number of Roses | Rose Size |
| Control with fertilizer only | 8 | 118 | 58 g | 4 | 34 | Average |
| Fertilizer with 2.5% oxy-prep 2.5% micro-prep | 8 | 137 | 72 g | 4 | 46 | Slightly bigger than control |

The results indicate that the fertilizers fortified with oxy-prep and micro-prep improved the number and size of tomatoes and roses.

Similar experiments were conducted with rice fields. In these experiments, one acre fields were selected. The results revealed roughly a 6.5% increase in harvested rice yield compared to the control field, where only fertilizer was used. In the experimental plot, oxy-prep and micro-prep were applied to the field at the rate of 0.5% each of the total amount of fertilizer. A possible explanation for the increase in yield could be enhanced aerobic bacterial growth due to continuous oxygenation from oxy-prep.

In a separate experiment, oxy-prep and micro-prep were applied to green turf as supplements to a normal fertilizer. Compared to turf treated with the fertilizer only, growth and color was better in the turf that was treated with oxy-prep and micro-prep. Used in hydroponic gardening, oxy-prep and micro-prep eliminated the necessity of pumping air into the water.

EXAMPLE 12

This experiment evaluated the effect on growth, production, general well being, and reduction of mortality of adding oxy-prep and micro-prep to feed for beef cattle, dairy cattle, poultry, dogs, cats, and pigs. The micro-prep was prepared according to the procedure described under Composition of Micro-Prep, above. The following microorganisms were grown individually: *Lactobacillus acidophilus, Lactobacillus casei, Lactobacillus plantarum, Pediococcus acidolatic, Lactococcus lactis* var. *lactis, Bifidobacterium bifidus, Lactococcus lactis* var Lactis subspecies *diacetylactis, streptococcus faecium, Propionibacterium shermanii, Propionibacterium arabinosum* and *Propionibacterium zeae, Saccharomyces cerevisiae, Aspergillus oryza* and *Bacillus subtilus*. At the end of the growth, the organisms were mixed together, forming a combined liquid culture. Ten gallons of the combined liquid culture was thoroughly mixed with the following ingredients to form a doughy mass: 1.0 pounds of lecithin, 0.1 pounds of sodium propionate, 2.0 pounds calcium carbonate, 2.0 pounds of multi-enzymes, 0.10 pounds of yucca schidigera extract (range 0.01 to 1 pound), 40 pounds of sodium bentonite (range 30 to 60 pounds), 20 pounds of rice flour (range 10 to 30 pounds), and 20 pounds of wheat flour. The pH of the mix was adjusted to 6.5 to 7.5 using sodium hydroxide or sodium bisulfate. The micro-prep was extruded in the form of small pellets. The extruded micro-prep was dried and milled to the consistency of the feed.

The oxy-prep was prepared using the following formula: urea—20 lbs; 2.5 to 10% hydrogen peroxide—100 lbs; lecithin—1 lb; vitamin C—20 grams; guar gum—1 lb; sodium bentonite (range 30 to 60 pounds)—40 lbs; perlite (range 5 to 15 pounds)—10 lbs; rice flour (range 30 to 50 pounds)—40 lbs. The mixture was extruded and dried at room temperature. At the end of the drying, the oxy-prep was milled to the consistency of the appropriate feed.

The micro-prep and oxy-prep thus prepared were mixed at the following micro:oxy ratios: 100:0; 0:100; 95:5; 90:10; 80:20; and 70:30. The above blended micro-prep and oxy-prep were included into the animal and poultry feeds according to the following formulas:

Dairy cattle feed—feed 99.75 lbs+0.25 lbs of 70:30 micro/oxy blend
Dairy cattle feed—feed 99.75 lbs+0.25 lbs of 80:20 micro/oxy blend
Dairy cattle feed—feed 99.75 lbs+0.25 lbs of 100:00 micro/oxy blend
Dairy cattle feed—feed 99.75 lbs+0.25 lbs of 00:100 micro/oxy blend
Beef cattle feed—feed 99.50 lbs+0.50 lbs of 90:10 micro/oxy blend
Calf starter feed—feed 99.95 lbs+0.05 lbs of 95:5 micro/oxy blend
Pig feed—feed 99 lbs+1 lb of 90:10 micro/oxy blend
Dog food—food 99.0 lbs+1.0 lbs of 95:5 micro/oxy blend
Cat food—food 98.0 lbs+2.0 lbs of 95:5 micro/oxy blend.

The above preparations were fed to the corresponding animals for a period of 1 to 3 months, during which time the following qualitative and quantitative observations and recordings were made: Milk production improved by 1% to 2%. Even though the result is not conclusive, the mastitis incidence was low with cows fed with micro-prep and oxy-prep. In each case when micro-prep and oxy-prep were included, the milk yield was better. Micro-prep and oxy-prep, individually, did not perform as well as the combined oxy-prep and micro-prep in the feed. However, micro-prep, alone, was superior to oxy-prep, alone. This result might be due to inclusion in the micro-prep of peroxide producing bacterium and catalase producing organisms. The weight gain in beef cattle was roughly 2.5%.

In the case of poultry, egg production improved by 2 to 3%. Also, the smell in the poultry sheds was less ammoniacal. Scours and diarrhea were reduced compared to the controls which received only the feed. Dogs and cats improved their general health and appearance. More significantly their faecal odors improved as compared to the controls.

While conducting animal feed tests, it was observed that the presence of oxy-prep and micro-prep in the silage appeared to improve the quality and flavor of the silage. Thus, it appears that treatment with these compositions can improve or preserve the quality of silage.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

We claim:

1. A moisture activated biochemical media system for reducing pollution or spoilage, comprising:
   (a) a first preparation of:
      (1) a moisture activated means for supplying a predetermined, water dispersible oxygen inducer; and
      (2) a first carrier means for carrying said means for supplying the predetermined oxygen inducer; and
   (b) a second preparation of:
      a biochemical oxygen-releasing means, reactive with said predetermined oxygen inducer in the presence of moisture for releasing nascent oxygen.

2. The media system of claim 1, wherein said predetermined oxygen inducer is selected from the group consisting of catalase enzyme, peroxidase enzyme, water-soluble peroxide destabilizing compounds or enzymes, and combinations thereof.

3. The media system of claim 1, wherein said oxygen-releasing means comprises a means for releasing a peroxide.

4. The media system of claim 1, wherein said oxygen-releasing means comprises:
   hydrogen peroxide in quantity from 0.01% to 50% by weight of the oxygen-releasing means; and
   urea in a quantity from 0.1 part to 3 parts per 1 part of hydrogen peroxide by weight.

5. The media system of claim 1, wherein said first carrier means comprises a pellet carrying said means for supplying the predetermined oxygen inducer as a portion thereof.

6. The media system of claim 5, wherein said pellet further comprises an enzyme selected from the group consisting of protease, lipase, amylase, cellulase, pectinase, glucose oxidase, galactose oxidase, lactase, and mixtures thereof.

7. The media system of claim 5, wherein said pellet further comprises vegetable flour.

8. The media system of claim 5, wherein said pellet further comprises a dairy by-product selected from the group consisting of whey, buttermilk, dry milk, whey protein concentrate, demineralized whey solids, lactose, milk permeates, cheese solids, dairy product solids, and mixture thereof.

9. The media system of claim 5, wherein said pellet is water soluble and further comprises a pellet binder stabilizing the pellet in water.

10. The media system of claim 9, wherein said binder is selected from the group consisting of lignin compounds, alginates, magnesium-calcium compounds, polymers, hydrocolloids, and mixtures thereof.

11. The media system of claim 5, wherein said pellet further comprises bentonite.

12. The media system of claim 1, wherein said an oxygen-releasing means is selected from the group consisting of hydrogen peroxide, magnesium peroxide, sodium peroxide, sodium percarbonate, carbamamide peroxide, and mixtures thereof.

13. The media system of claim 1, wherein said oxygen-releasing means further comprises a stabilizing means for preventing release of oxygen without exposure to said oxygen inducer.

14. The media system of claim 13, wherein said stabilizing means comprises a proteinaceous material selected from the group consisting of urea, nonfat dry milk, casein, caseinates, whole cell yeast, yeast extract, vegetable protein, gum and mixtures thereof.

15. The media system of claim 13, wherein said stabilizing means comprises a sugar selected from the group consisting of glucose, galactose, lactose, and mixtures thereof.

16. The media system of claim 1, wherein said oxygen-releasing means further comprises an emulsifier.

17. The media system of claim 1, wherein said oxygen releasing means further comprises lecithin in quantity range from 0.05% to 3.0% by weight.

18. The media system of claim 1, wherein said an oxygen-releasing means comprises a substrate-enzyme mixture generating hydrogen peroxide upon exposure to moisture.

19. The media system of claim 18, wherein said substrate-enzyme mixture is selected from the group consisting of glucose and glucose oxidase, galactose and galactose oxidase, and mixtures thereof.

20. The media system of claim 1, wherein said means for supplying oxygen inducer comprises a viable micro-organism capable of producing said oxygen inducer by metabolism.

21. The media system of claim 20, wherein said micro-organism is selected from the group consisting of catalase positive micro-organisms, peroxide positive micro-organisms, and mixtures thereof.

22. The media system of claim 20, wherein said first preparation comprises micro-organisms selected from the group consisting of genus Propionibacterium, Bacillus, Nitrobacter, Nitrosococcus, Nitrosomonas, Rhizobium, Penicillium, Pediococcus, Leuconostoc, Aspergillus, Streptococcus, Lactococcus, Lactobacillus, Thiobacillus, Pseudomonas, Brevibacterium, Saccharomyces and mixtures thereof.

23. The media system of claim 20, wherein said micro-organism is selected from the group consisting of lactose negative bacteria, casein negative bacteria, lactose negative mutant bacteria, casein negative mutant bacteria, and mixtures thereof.

24. The media system of claim 1, wherein said means for supplying the oxygen inducer comprises a water soluble, solid particle of said oxygen inducer.

25. The media system of claim 1, further comprising aquatic animal feed.

26. The media system of claim 25, wherein said aquatic animal feed is selected from the group consisting of shrimp feed and fish feed.

27. The media system of claim 25, wherein said aquatic animal feed comprises a means for buffering pH in the range from 7.0 to 9.0.

28. The media system of claim 27, wherein said buffering means is selected from the group consisting of sodium montmorillonite, sodium carbonate, sodium bicarbonate, zeolite, smectite, magnasite, perlite, and mixtures thereof.

29. The media system of claim 25, further comprising a means for reducing algae and phytoplankton.

30. The media system of claim 29, wherein said means for reducing algae and phytoplankton is selected from the group consisting of acid blue #9 dye, chelated copper sulfate, and mixtures thereof.

31. The media system of claim 1, wherein:
said first preparation is of specific gravity greater than water, whereby the first preparation is sinkable in water; and
wherein said second preparation further comprises:
a second carrier means for carrying said oxygen-releasing means;
wherein the second preparation is of specific gravity greater than water, whereby the second preparation is sinkable in water;
whereby the first and second preparations are placeable in mutual proximity near the bottom of a body of water.

32. The media system of claim 31, wherein said second carrier means comprises substantially metal-free silica.

33. The media system of claim 31, wherein said second carrier means comprises a pellet carrying said oxygen-releasing means as a portion thereof.

34. The media system of claim 31, wherein said second carrier means further comprises a binder of hydrocolloid material at a concentration of 0.1% to 2.5% by weight.

35. The media system of claim 34, wherein said binder comprises a gum.

36. The media system of claim 31, wherein said second carrier means further comprises vegetable flour in quantity of from 10% to 80% by weight.

37. The media system of claim 31, further comprising a means for digesting dead algae and phytoplankton.

38. The media system of claim 37, wherein said means for digesting dead algae and phytoplankton is selected from the group consisting of micro-organisms, rotofers, and mixtures thereof.

39. The media system of claim 1, wherein:
said first preparation comprises a mixture of enzymes and nutrients in combination with micro-organisms selected from the group consisting of catalase positive micro-organisms, catalase negative micro-organisms, proteolytic micro-organisms, lipolytic micro-organisms, cellulytic micro-organisms, starch digesting micro-organisms, and mixtures thereof; and
said second preparation comprises a dry blend of components selected from the group consisting of sodium percarbonate, sodium bicarbonate, sodium bisulfate, metallic aluminum, aluminum salts, calcium carbonate, and mixtures thereof.

40. The media system of claim 39, wherein said enzymes are selected from the group consisting of lipase, protease, amylase, cellulase, pectinase, and mixtures thereof.

41. The media system of claim 39, wherein said microorganisms are selected from the group consisting of Streptococcus, Pseudomonas, yeast, molds, Bacillus, and mixtures thereof.

42. The media system of claim 39, wherein said microorganisms are selected from the group consisting of lactose negative microorganisms, casein negative micro-organisms, and mixtures thereof.

43. The media system of claim 1, further comprising lactoperoxidase and a thiocyanate salt.

44. The media system of claim 1, adapted for use in animal feeds, fertilizer and silage, wherein:

said means for supplying predetermined oxygen-inducer comprises peroxide cleaving enzyme positive microorganisms; and said first carrier means comprises a combination of bentonite, pH adjusting means, stabilizing means, buffer, enzymes, nutrients, and yucca schidigera extract.

* * * * *